United States Patent
Teirstein et al.

(10) Patent No.: US 8,206,321 B2
(45) Date of Patent: Jun. 26, 2012

(54) GUIDE WIRE LOADING METHOD AND APPARATUS

(75) Inventors: Paul S. Teirstein, LaJolla, CA (US); Osama Amine, Newark, NJ (US)

(73) Assignee: Paul S. Teirstein, La Jolla, CA (US)

(*) Notice: Subject to any disclaimer, the term of this patent is extended or adjusted under 35 U.S.C. 154(b) by 285 days.

(21) Appl. No.: 12/218,031

(22) Filed: Jul. 9, 2008

(65) Prior Publication Data
US 2010/0010376 A1 Jan. 14, 2010

(51) Int. Cl.
*A61B 5/00* (2006.01)
*A61M 25/00* (2006.01)
*A61F 11/00* (2006.01)

(52) U.S. Cl. ......... 600/585; 604/523; 604/528; 606/108

(58) Field of Classification Search .................. 600/523, 600/528, 585; 604/523, 528; 606/108
See application file for complete search history.

(56) References Cited

U.S. PATENT DOCUMENTS

| | | | |
|---|---|---|---|
| 4,185,636 A | 1/1980 | Gabbay et al. | |
| 4,336,806 A | 6/1982 | Eldridge, Jr. | |
| 4,492,229 A | 1/1985 | Grunwald | |
| 4,820,274 A | 4/1989 | Choksi et al. | |
| 4,903,826 A * | 2/1990 | Pearce | 206/63.3 |
| 4,907,332 A * | 3/1990 | Christian et al. | 29/237 |
| 5,735,821 A * | 4/1998 | Dobkin | 604/174 |
| 5,830,157 A * | 11/1998 | Foote | 600/585 |
| 5,978,699 A * | 11/1999 | Fehse et al. | 600/434 |
| 6,190,333 B1 * | 2/2001 | Valencia | 600/585 |
| 6,511,470 B1 * | 1/2003 | Hamilton | 604/528 |
| 6,554,808 B1 * | 4/2003 | Cook | 604/265 |
| 6,872,192 B2 * | 3/2005 | Nash et al. | 604/164.02 |
| 7,303,568 B2 | 12/2007 | Jannot | |
| 2002/0177789 A1 | 11/2002 | Ferry et al. | |
| 2005/0182368 A1 | 8/2005 | Gillis et al. | |
| 2006/0149292 A1 | 7/2006 | Knudtson et al. | |
| 2006/0253048 A1 | 11/2006 | Jones et al. | |
| 2007/0118079 A1 | 5/2007 | Moberg et al. | |
| 2009/0157089 A1 * | 6/2009 | Plans | 606/108 |

* cited by examiner

*Primary Examiner* — Max Hindenburg
*Assistant Examiner* — Devin Henson
(74) *Attorney, Agent, or Firm* — Mark D. Wieczorek; Mayer & Williams PC

(57) ABSTRACT

A device for loading a guide wire into the open end of a tubular instrument such as a catheter. The device can be a block of material having a groove in its surface. The ends of the guide wire and the tubular instrument are placed into the groove and moved toward each other. When the ends meet, the groove guides the guide wire into the open end of the tubular instrument. The groove, or at least a portion of the groove, can have a cross-sectional contour that closely matches the outside radius of the tubular instrument. The groove can have one portion with a shallower depth than the other portion, with the guide wire run in the shallower portion and the tubular instrument in the deeper portion. The guide wire and the tubular instrument can be angled above the device, with just their ends moving along the groove.

14 Claims, 3 Drawing Sheets

GUIDE WIRE LOADING METHOD AND APPARATUS

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention is in the field of equipment used for intravascular medical procedures, such as guide wires, stents, angioplasty balloons, drilling burrs, and the catheters that are used to convey some of these.

2. Background Art

In the field of interventional cardiology, catheters and other tubular instruments are often run into a blood vessel by being threaded over a guide wire that has been placed into the blood vessel. So, it is often necessary to thread a very small diameter guide wire into the open end of a very small tubular instrument. The guide wires are usually about 0.014 inches in diameter, and the tubular instruments into which they are threaded can have diameters ranging from about 2 to 4 French. Catheters are often used to convey and operate various other types of instruments, such as balloons, stents, burrs, or radioactive segments. Many of these are also tubular in shape, and guide wires are often threaded through them. Because of the small diameters of the catheters, these other instruments, and the guide wires, it is very difficult to see and manipulate these members well enough to thread the guide wire into the tubular instrument very quickly. The speed and efficiency of every movement are important in interventional cardiology and other disciplines, as the blood flow in the blood vessel being used is often compromised.

It is the object of the present invention to provide a device, and a method for its use, which will quickly and efficiently thread a very small diameter guide wire into a very small diameter tubular instrument, such as a catheter.

BRIEF SUMMARY OF THE INVENTION

The present invention is a device for loading a guide wire into the open end of a tubular instrument such as a catheter. The device can be a block of material which has an open groove in its surface. The end of the guide wire and the open end of the tubular instrument are placed into the groove, and the two ends are moved toward each other. The guide wire and the tubular instrument can be angled above the device, with just their ends moving along the groove. When the ends meet, the groove guides the guide wire into the open end of the tubular instrument.

The groove, or at least a portion of the groove, can have a cross-sectional contour that closely matches the outside radius of the tubular instrument. The bottom of the groove is basically a concave surface. The bottom of the groove can have a radiused or rounded cross-sectional contour, or it can be formed by a plurality of substantially flat longitudinal surfaces intersecting at shallow angles, thereby approximating a rounded contour. In this case, the spaces created by the joints between the flat surfaces, between the groove surface and the catheter, must be small enough to prevent entry of the end of the guide wire between the catheter and the groove surface. The radius and depth of the rounded or multi-surfaced contour can be sized to work best with any selected diameter of tubular instrument.

The groove can have a uniform depth and cross-sectional radius along its entire length. The groove also can be split into two end-to-end segments, with one segment or portion having a shallower depth, and/or a smaller radius, than the other segment or portion, thereby forming a discontinuity in the depth, and/or the radius, of the groove where the two portions meet. In this case, the guide wire is run in the shallower, and/or smaller radiused, portion of the groove, and the tubular instrument is run in the deeper, and/or larger radiused, portion. Preferably, the tubular instrument would first be run along the deeper, and/or larger radiused, portion of the groove until it butts up against the discontinuity in depth, and/or radius, where the two portions of the groove meet. Then, the guide wire would be run along the shallower, and/or smaller radiused, portion of the groove until its end enters the open end of the tubular instrument.

The device also can have a plurality of grooves on its surface, with each groove having a different depth, and/or cross-sectional radius, to make it substantially match the radius of a different diameter tubular instrument. Each groove can be labeled as to the size of tubular instrument with which it can best be used. Grooves having two different depths, and/or cross-sectional radii, can be so labeled.

The inner surface of the groove can have a slick surface, either because of the material from which the device is formed, the smoothness of the surface, or because of lubrication on the surface.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
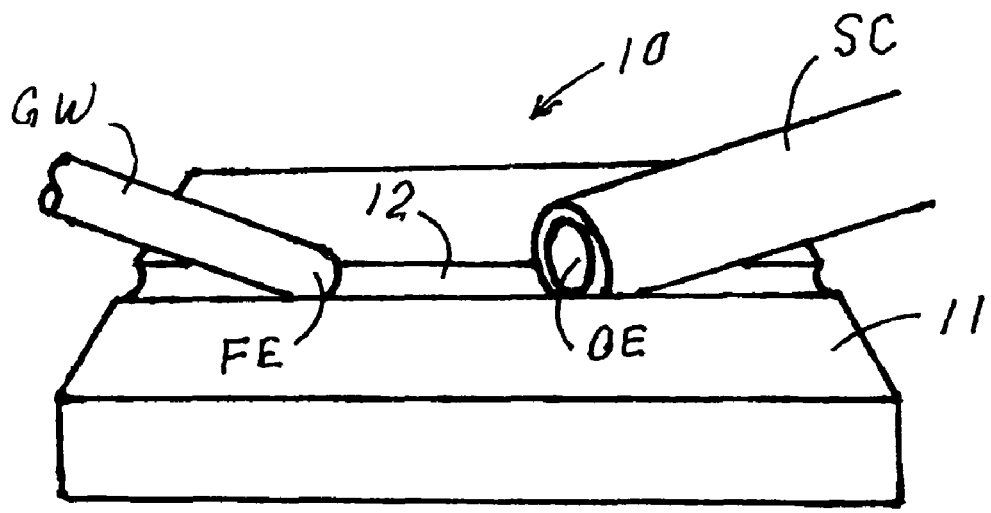
FIG. 1 is a perspective view of a device according to the present invention, in use with a guide wire and a catheter.

As shown in FIG. 1, a device 10 according to the present invention comprises a body 11 made of any appropriate material, such as a plastic or metal. Formed within at least one surface of this body 11 is at least one open groove 12. Various possible characteristics of the groove 12 are discussed below. In use, a guide wire GW has been introduced into a blood vessel of a patient (not shown). The free end FE of the guide wire GW is placed in the groove 12. The guide wire is held so that it is angled relative to the surface of the body 11, for example, at a 45 degree angle, as its free end FE is placed and held in the groove 12. A selected catheter SC is also held so that it is angled at a similar angle relative to the surface of the body 11, oriented toward the groove 12, and an open end OE of the catheter SC is placed in the groove 12. Rather than a catheter, any other type of tubular instrument may also be used with the present invention. The catheter, or any other tubular instrument for that matter, is referred to herein as a "selected" catheter, because it is selected for use in the medical procedure, at least partially because of its outside diameter. The groove 12 is designed to have dimensions that will function best with this selected outside diameter of the selected catheter SC. Once the respective ends FE, OE of the guide wire GW and the selected catheter SC are placed within the groove 12, the guide wire GW and the catheter SC are moved toward each other. Alternatively, one member may be held stationary, and the other member may be moved toward it. What matters is that the ends FE, OE of the two members are brought together in the groove 12. When the two ends FE, OE meet, the free end FE of the guide wire GW will enter the open end OE of the catheter SC, with both being guided by the groove 12.

It is usually helpful if the surface of the groove 12 is made "slick", either by being made very smooth, or by being lubricated, or both. In order to achieve lubrication, the body 11 of the device 10 may be formed of a lubricious material, such as various types of plastic, or lubrication can be provided by application of a lubricant in the groove 12 or on the guide wire GW. Application of a liquid to the groove 12 may also be beneficial, in that the surface tension of the liquid may assist in guiding the guide wire GW into the selected catheter SC.

Figure 2:
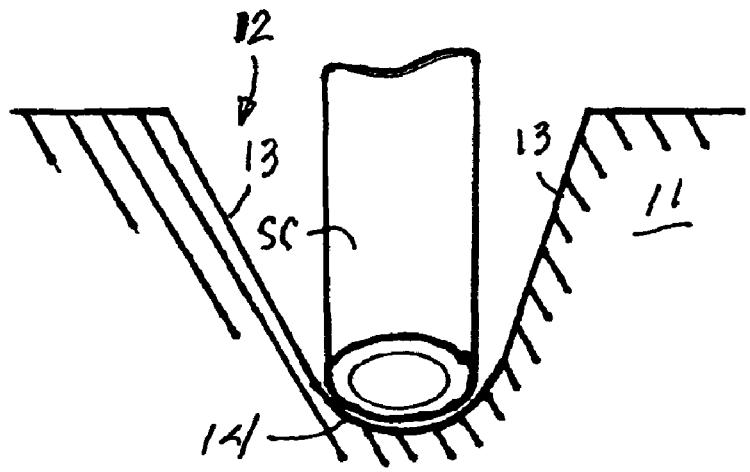
FIG. 2 is a sectional view of one type of cross-sectional contour that may be used in the invention of FIG. 1.

The groove 12 may have several different types of cross section and various depths. As shown in FIG. 1, the groove 12 may be substantially a semi-circular groove in the surface of the body 11. Alternatively, as shown in FIG. 2, the groove 12 may have sides 13 that taper inwardly toward a substantially concave cross-sectional contour 14 at the apex, or bottom, of the tapered groove 12. In FIG. 2, the concave contour is actually rounded, having a radius that substantially matches the outside radius of the catheter SC. It can also be seen that, while in FIG. 1, the groove 12 has a depth that is less than the outside diameter of the catheter SC, FIG. 2 shows that the groove 12 can alternatively have depth that is greater than the outside diameter of the catheter SC.

Figure 3:
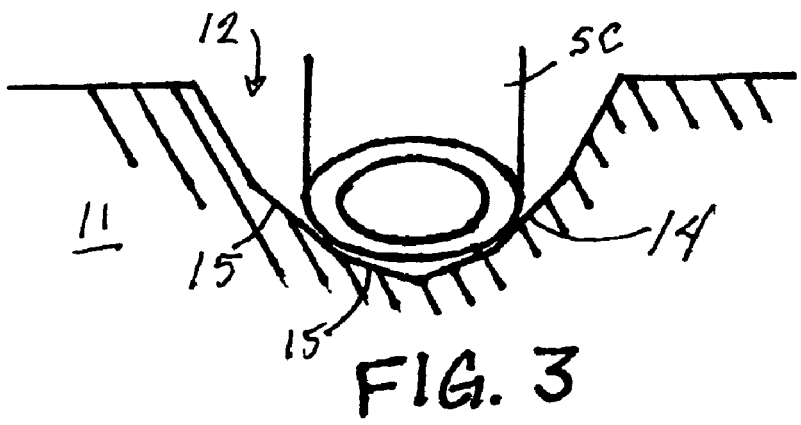
FIG. 3 is a sectional view of a second type of cross-sectional contour that may be used in the invention of FIG. 1.

FIG. 3 illustrates that, rather than having a rounded cross-sectional contour, the concave contour 14 at the bottom of the groove 12 can also be formed by a plurality of other surfaces, such as longitudinally arranged substantially flat surfaces 15 within the groove 12, with the flat surfaces forming a contour approximating a radiused curve. It is important that the spaces created by the joints between the flat surfaces, between the groove surface and the catheter, must be small enough to prevent entry of the end of the guide wire between the catheter and the groove surface. That is, the flat surfaces must be sufficiently narrow, and appropriately angled, to insure that the space between the flat groove surfaces and the catheter is less than the diameter of the guide wire. FIG. 3 also shows that this approximate radiused curve can also have a radius that substantially matches the outside radius of the catheter SC. Whether the concave contour 14 is round or formed from a plurality of flat surfaces, it is preferred that the concave contour 14 have a radius that is substantially the same as the outside radius of the catheter SC, plus or minus 10% of the catheter radius. Ideally, the concave contour 14 will have a radius that is no less than the outside radius of the catheter SC, and no greater than the outside radius of the catheter SC plus 10% of the catheter radius.

Figure 4:
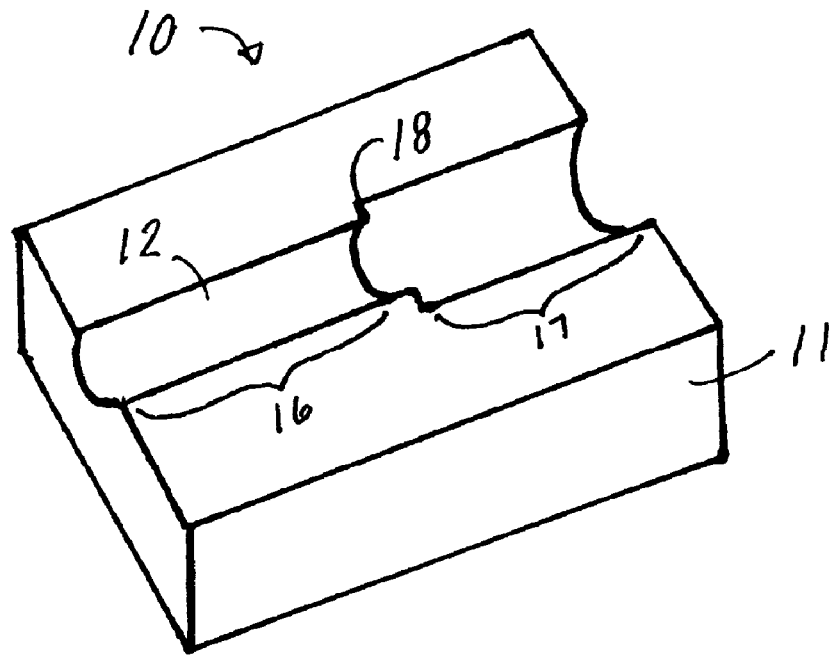
FIG. 4 is a perspective view of a second embodiment of a device according to the present invention.
Figure 5:
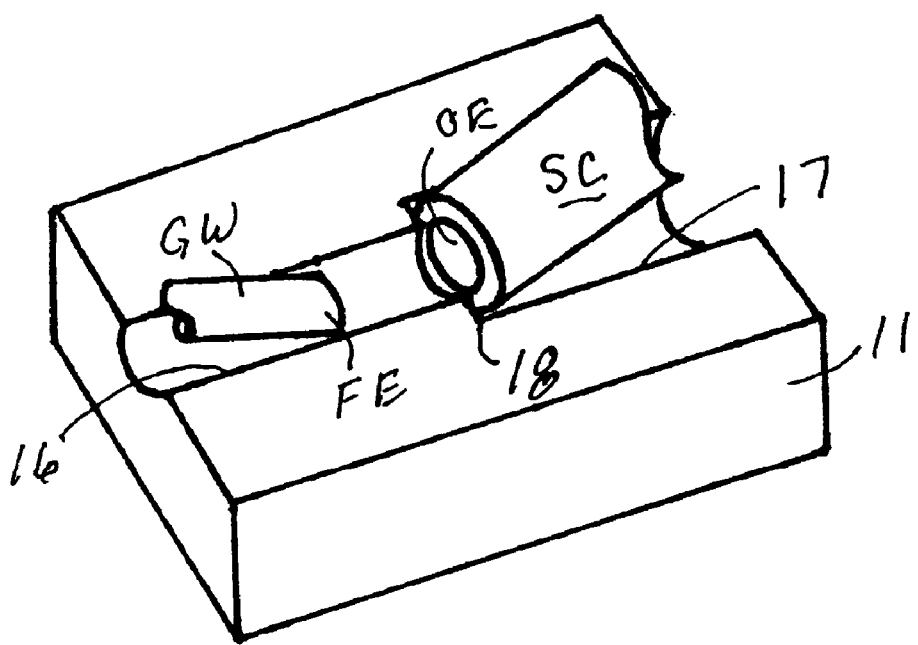
FIG. 5 is a perspective view of the embodiment of FIG. 4 in use with a guide wire and a catheter.

As shown in FIG. 4, the groove 12 can have two segments or portions 16, 17, with a first segment 16 having a shallower depth and/or a smaller radius than the second segment 17. This forms a discontinuity 18 at the point where the two groove portions 16, 17 meet, end-to-end. At the discontinuity 18, the depth and/or radius of the groove 12 change from the shallower depth and/or smaller radius of the first portion 16 to the deeper depth and/or larger radius of the second portion 17. It is also usually advantageous to have the center of radius, or axis, of the first portion 16 of groove 12 aligned with the center of radius, or axis, of the second portion 17 of the groove 12. FIG. 5 shows this embodiment of the invention 10 in use. First, the open end OE of the selected catheter SC is placed in the second portion 17 of the groove 12, and the open end OE of the selected catheter SC is slid along this deeper/larger radiused portion 17 of the groove 12, until the open end OE abuts the discontinuity 18. Then, the free end FE of the guide wire GW is placed in the first portion 16 of the groove 12, and the free end FE of the guide wire GW is slid along this shallower/smaller radiused portion 16 of the groove 12, until the free end FE of the guide wire GW enters the open end OE of the selected catheter SC. In some applications, having this disparity between the depths and/or radii of the two portions 16, 17 of the groove 12 makes it easier to thread a guide wire GW into a selected catheter SC, or some other tubular instrument.

Figure 6:
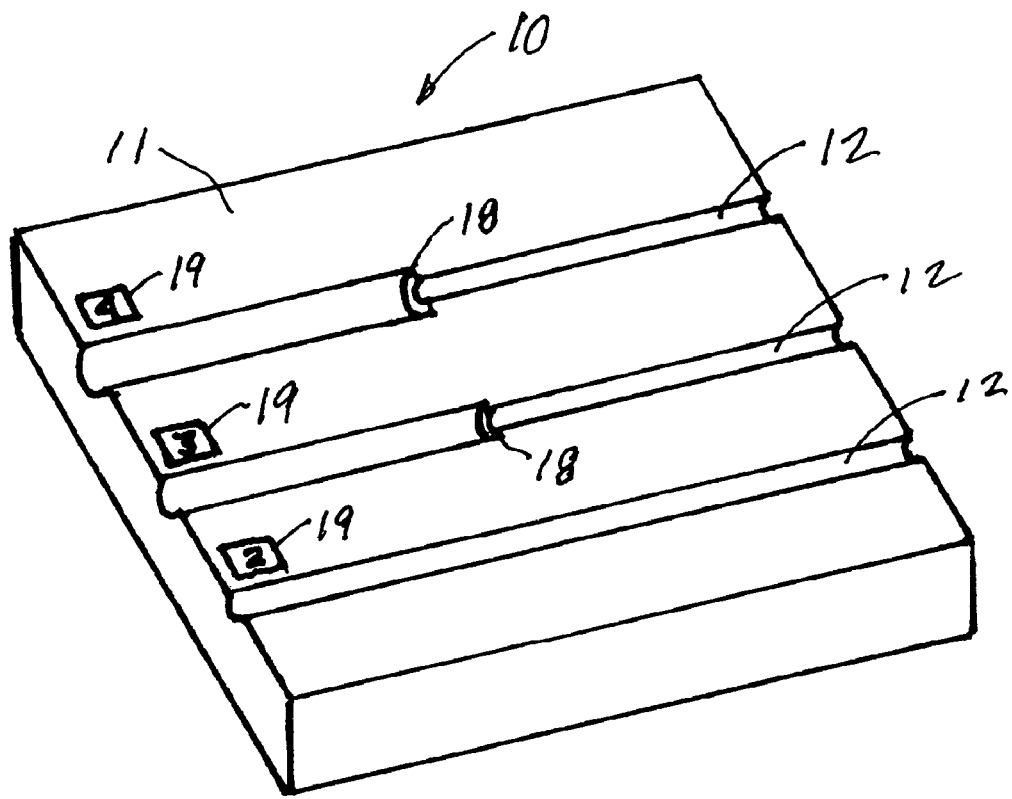
FIG. 6 is a perspective view of a third embodiment of a device according to the present invention.

FIG. 6 illustrates that the device 10 can have a plurality of open grooves 12 in the body 11. Each of the grooves 12 can be formed with a different depth and/or a different radius on its bottom contour. Some grooves 12 may have discontinuities 18, and others may be continuous. Each groove 12 should have a label 19 which can indicate the depth, bottom contour shape, or radius of the groove, as well as whether the groove 12 is continuous or has a discontinuity 18.

Figure 7:
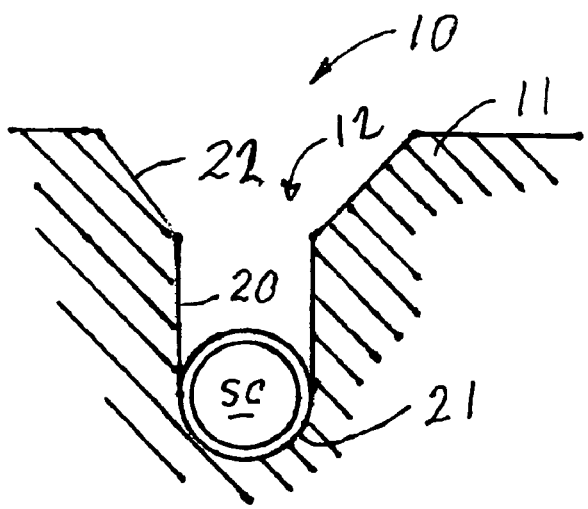
FIG. 7 illustrates a profile of an exemplary groove according to the present invention.

It has been found that the present invention functions in an optimum fashion if the shape of at least the catheter portion of the groove 12 has certain specific characteristics. While these characteristics are not critical to the invention, they add to its functionality. Specifically, as shown in FIG. 7, the groove 12 can have a bottom profile consisting of vertical sides 20 culminating in a rounded contour 21. The upper profile consists of sloped sides 22 that taper inwardly from the surface of the body 11 toward the upper ends of the vertical sides 20. The rounded contour 21 has a diameter that is the same as the outer diameter of the catheter SC. As a result, this rounded contour 21 makes full contact with a 180 degree radius of the periphery of the catheter SC, thereby gripping the catheter SC securely, but not impeding placement of the catheter SC into the groove 12. The vertical sides 20 extend upwardly from there. The full depth of the bottom profile of the groove 12, including the vertical sides 20 and the rounded contour 21, is approximately twice the diameter of the selected catheter SC. The sloped sides 22 assist in placing the catheter SC into the bottom profile 20, 21 of the groove 12.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A medical device for loading a medical guide wire into a selected tubular medical instrument having a selected outside radius, said loading device comprising:
   a body having a flat surface; and
   a plurality of open grooves formed in the flat surface of said body for receiving medical guidewires and tubular medical instruments;

wherein each of said plurality of open grooves further comprises:
  sides that extend within said body and from said flat surface of said body; and
  a rounded contour at the bottom of said sides, said rounded contour having a cross section with a radius that matches said outside radius of said selected tubular medical instrument to within plus or minus 10%; and
wherein said sides and said rounded contour of said open groove have a combined depth greater than the outside diameter of said selected tubular instrument;
wherein at least one but not all of said plurality of open grooves includes a first portion having a shallower depth than a second portion of said at least one of said plurality of open grooves, said first portion of said groove having a first rounded contour with a smaller radius than a second rounded contour in said second portion of said groove; and
wherein a different rounded contour is formed in each of at least two of said plurality of grooves, said different contours corresponding to the outside radii of a plurality of different sized selected tubular medical instruments.

2. The medical device recited in claim 1, wherein each said groove in said body has a different rounded contour formed therein.

3. The medical device recited in claim 1, further comprising a label associated with each said groove, each said label indicating the outside radius of a selected tubular medical instrument with which said rounded contour in its associated said groove will match.

4. The medical device recited in claim 1, further comprising a smooth surface within said at least one open groove.

5. The medical device recited in claim 1, further comprising a lubricant within said at least one open groove.

6. The medical device recited in claim 1, wherein said second rounded contour in said second portion of said groove matches said outside radius of said selected tubular medical instrument to within plus or minus 10%.

7. The medical device recited in claim 6, wherein said first rounded contour in said first portion of said groove has a center of radius which is aligned with a center of radius of said second rounded contour in said second portion of said groove.

8. The medical device recited in claim 1, further comprising:
  a first cross-sectional radius formed inside said rounded contour of at least one of said plurality of grooves; and
  a second cross-sectional radius formed on the outside of said selected medical tubular instrument;
    wherein said first radius matches said second radius to within plus or minus 10%.

9. The medical device recited in claim 8, wherein said first radius is no smaller than said second radius and no more than 10% larger than said second radius.

10. The medical device recited in claim 1, wherein said sides further comprise:
  an inwardly tapered section extending from said flat surface of said body; and
  vertical sides below said inwardly tapered section.

11. The medical device recited in claim 10, wherein said vertical sides and said rounded contour of said open groove have a combined depth equal to twice the outside diameter of said selected tubular medical instrument.

12. A method for loading a medical guide wire into a selected tubular medical instrument, said method comprising:
providing a medical device having a body with a flat surface and having a plurality of open grooves formed within the body and extending into the body from the flat surface, said plurality of open grooves each having a concave contour shaped to match an outside radius of said selected tubular medical instrument to within plus or minus 10%, and wherein each of said plurality of open grooves further comprises sides that extend within the body from said flat surface and a rounded contour at the bottom of said sides, said rounded contour having a cross section with a radius that matches said outside radius of said selected tubular medical instrument to within plus or minus 10%, and wherein said sides and said rounded contour of said open groove have a combined depth greater than the outside diameter of said selected tubular medical instrument, and wherein a first portion of at least one groove but not all of said plurality of open grooves has a shallower depth than a second portion of said plurality of open grooves, and said first portion of said groove has a first rounded contour with a smaller radius than a second rounded contour in said second portion of said groove, and wherein a different rounded contour is formed in each of at least two of said plurality of grooves, said different contours corresponding to the outside radii of a plurality of different sized selected tubular medical instruments;
placing an open end of said tubular medical instrument in one groove of said plurality of grooves;
placing an end of said medical guide wire in said groove;
holding said tubular medical instrument angled above said flat surface of said medical device, with said open end of said tubular medical instrument in said groove;
holding said medical guide wire angled above said surface of said medical device, with said end of said medical guide wire in said groove; and
moving said medical guide wire and said tubular medical instrument toward each other, while maintaining said medical guide wire and said tubular medical instrument angled above said flat surface, until said end of said medical guide wire enters said open end of said tubular medical instrument.

13. The method recited in claim 12, further comprising:
placing said end of said medical guide wire in said first portion of said groove;
placing said open end of said tubular medical instrument in said second portion of said groove, the first and second portions of said open groove creating a depth discontinuity where said first portion of said groove meets said second portion of said groove;
moving said open end of said tubular medical instrument along said second portion of said groove toward said first portion of said groove until said open end of said tubular medical instrument abuts said depth discontinuity between said two portions of said groove; and
moving said medical guide wire along said first portion of said groove toward said second portion of said groove until said end of said medical guide wire enters said open end of said tubular medical instrument.

14. A medical device for loading a medical guide wire into a selected tubular medical instrument having a selected outside radius, said medical loading device comprising:
a body having a flat surface; and
a plurality of open grooves formed in the flat surface of said body;
  wherein each of said plurality of open grooves further comprises:

sides that extend within said body and from said flat surface of said body; and a rounded contour at the bottom of said sides, said rounded contour having a cross section with a radius that matches said outside radius of said selected tubular instrument to within plus or minus 10%; and wherein said sides and said rounded contour of said open groove have a combined depth greater than the outside diameter of said selected tubular medical instrument;

wherein at least two of said plurality of open grooves include first portions having shallower depths than second portions, said first portions of said open grooves having a first rounded contour with a smaller radius than a second rounded contour in said second portions of said open grooves, and wherein said at least two of said plurality of open grooves include a commonly-sized first rounded contour; and wherein a different rounded contour is formed in each of at least two of said plurality of open grooves, said different contours corresponding to the outside radii of a plurality of different sized selected tubular medical instruments.

* * * * *